(12) United States Patent
Zografos et al.

(10) Patent No.: US 10,926,264 B2
(45) Date of Patent: Feb. 23, 2021

(54) DISPENSING SYSTEM FOR APPLYING DNA TAGGANTS USED IN COMBINATIONS TO TAG ARTICLES

(71) Applicant: SafeTraces, Inc., Oakland, CA (US)

(72) Inventors: Antonios Zografos, Oakland, CA (US); Laurie M. Clotilde, Hayward, CA (US)

(73) Assignee: SafeTraces, Inc., Pleasanton, CA (US)

( * ) Notice: Subject to any disclaimer, the term of this patent is extended or adjusted under 35 U.S.C. 154(b) by 400 days.

(21) Appl. No.: 15/867,441

(22) Filed: Jan. 10, 2018

(65) Prior Publication Data
US 2019/0211324 A1 Jul. 11, 2019

(51) Int. Cl.
*B01L 3/00* (2006.01)
(52) U.S. Cl.
CPC ......... *B01L 3/527* (2013.01); *B01L 2200/141* (2013.01); *B01L 2200/16* (2013.01)
(58) Field of Classification Search
CPC ................. C12N 15/1065; B01L 3/527; B01L 2200/141; B01L 2200/16; G05B 15/02; B05B 12/14
See application file for complete search history.

(56) References Cited

U.S. PATENT DOCUMENTS 4,593,360 A * 6/1986 Cocks ................. B05B 13/0452
118/696
6,312,911 B1 11/2001 Bancroft et al.
8,293,535 B2 10/2012 Farquar et al.
2002/0129523 A1 9/2002 Hunt
2004/0166520 A1 8/2004 Connolly
(Continued)

FOREIGN PATENT DOCUMENTS

WO 2008137831 A1 11/2008
WO 2011163296 A2 12/2011
(Continued)

OTHER PUBLICATIONS

Andrews, "DNA Spray-On Technology Could Revolutionize Food Traceability," Food Safety News, http://www.foodsafetynews.com/2014/11/dna-laced-spray-technology-could-revolutionize-food-traceability/#.W1kRNNVKjRY, Nov. 17, 2014, 2 pages.
(Continued)

*Primary Examiner* — Samuel P Siefke
*Assistant Examiner* — Quocan B Vo
(74) *Attorney, Agent, or Firm* — Haynes and Boone, LLP.

(57) ABSTRACT

A dispersant system comprises a plurality of taggant vessels, each having a taggant that corresponds to a position in a tag string and a computer controller convert the tag string into a selection of a taggant set while computer-controlled valves allow or block a flow of taggants to a manifold output tube. From the output tube, a mix of the taggants flow to form a dispersant formed according to the tag string. A nozzle disperses the dispersant onto an object to be tagged, possibly atomized with air. The taggant can comprise a DNA taggant comprising a static portion and a dynamic portion that is unique to each tag string position. Tag strings for adjacent lots might have a low Hamming distances to reduce cross-contamination and/or have redundancy for error detection and correction and selected so that consumption of taggants evens out over the plurality of taggant vessels.

19 Claims, 9 Drawing Sheets

(56) References Cited

U.S. PATENT DOCUMENTS

| | | | |
|---|---|---|---|
| 2006/0037222 A1* | 2/2006 | Hunt | G06K 19/06009 40/326 |
| 2010/0261193 A1 | 10/2010 | Webster et al. | |
| 2011/0177539 A1 | 7/2011 | Sutton et al. | |
| 2012/0112883 A1 | 5/2012 | Wallace et al. | |
| 2013/0052751 A1 | 2/2013 | Farquar et al. | |
| 2013/0122807 A1 | 5/2013 | Tenarvitz et al. | |
| 2014/0057276 A1 | 2/2014 | Farquar et al. | |
| 2014/0220576 A1 | 8/2014 | Macula | |
| 2014/0255984 A1 | 9/2014 | Sharpin | |
| 2014/0272097 A1* | 9/2014 | Jung | B41J 2/01 427/2.1 |
| 2014/0340423 A1 | 11/2014 | Taylor et al. | |
| 2015/0034309 A1 | 2/2015 | Blair | |
| 2015/0322426 A1 | 11/2015 | Zografos | |
| 2015/0361490 A1 | 12/2015 | Farquar et al. | |
| 2016/0102335 A1 | 4/2016 | Franciskovich et al. | |
| 2016/0171179 A1 | 6/2016 | Donofrio et al. | |
| 2016/0188943 A1 | 6/2016 | Franz | |
| 2017/0038353 A1 | 2/2017 | Zografos et al. | |
| 2017/0197002 A1 | 7/2017 | Dobrinsky et al. | |
| 2017/0322701 A1 | 11/2017 | Bowman et al. | |
| 2017/0333859 A1* | 11/2017 | Lind | B05B 12/1472 |
| 2018/0252738 A1 | 9/2018 | Denney | |

FOREIGN PATENT DOCUMENTS

| | | | |
|---|---|---|---|
| WO | 2014164958 A1 | 10/2014 | |
| WO | 2017049160 A2 | 3/2017 | |

OTHER PUBLICATIONS

Busta et al., "The Use of Indicators and Surrogate Microorganisms for the Evaluation of Pathogens in Fresh and Fresh-Cut Produce," Comprehensive Reviews in Food Science and Food Safety, 2(s1), Jan. 2003, pp. 179-185.

Bystrykh, "Generalized DNA Barcode Design Based on Hamming Codes," PLOS ONE 7(5):e36852, May 17, 2012, 8 pages.

Danyluk et al., "Process Validation: Selection and Use of Surrogates," University of Florida Institute of Food and Argicultural Sciences, presentation dated Apr. 2014, 19 pages.

Farquar, "DNATrax (DNA Tagged Reagents for Aerosol eXperiments)," Lawrence Livermore National Laboratory, presentation LLNL-PRES-642415, Aug. 2013, retrieved from the internet at <http://web.archive.org/web/20160226230017/https://ipo.llnl.gov/technologies/individual-tech-discovery&p=DNATrax>, 6 pages.

Hou et al., "Rapid bioparticle concentration and detection by combining a discharge driven vortex with surface enhanced Raman scattering," Biomicrofluids 1.014106:1-13, Feb. 16, 2007.

International Search Report and Written Opinion dated Sep. 8, 2016, International Patent Application No. PCT/US2016/038083, filed Jun. 17, 2016.

Ma et al., "Development of Thermal Surrogate Microorganisms in Ground Beef for In-Plant Critical Control Point Validation Studies," Journal of Food Protection, 70(4), Apr. 2007, pp. 952-957.

Naaum, "Novel Methods of Species and Product Authenticity and Traceability Testing Using DNA Analysis for Food and Agricultural Applications," Doctoral Dissertation, Department of Integrative Biology University of Guelph, Apr. 2014, 144 pages.

Niebuhr et al., "Evaluation of non-pathogenic surrogate bacteria as process validation indicators for *Salmonella enteric* for selected antimicrobial treatments, cold storage and fermentation in meat," Journal of Food Protection, 71(4), Apr. 2008, pp. 714-718.

Puddu et al., "Magnetically Recoverable, Thermostable, Hydrophobic DNA/Silica Encapsulates and Their Application as Invisible Oil Tags," ACS Nano 8(3):2677-2685, Feb. 25, 2014.

Sinclair et al., "A Criteria for Selection of Surrogates Used to Study the Fate and Control of Pathogens in the Environment," Applied and Environmental Microbiology, 78(6), published online Jan. 13, 2012, published in print Mar. 2012, pp. 1969-1977.

Yeater et al., "Effectiveness of Sanitzing Products on Controlling Selected Pathogen Surrogates on Retail Deli Slicers," Journal of Food Protection, 78(4), Apr. 2015, pp. 707-715.

Harding et al., "Unique DNA-barcoded aerosol test particles for studying aerosol transport," Aerosol Science and Technology 50(5):429-435, Mar. 22, 2016.

International Search Report and Written Opinion dated Aug. 8, 2019, International Patent Application No. PCT/US2019/029002, filed Apr. 24, 2019, 8 pages.

International Search Report and Written Opinion, dated Mar. 15, 2019, International Patent Applicaton No. PCT/US19/13069, filed Jan. 10, 2019, 13 pages.

Sharma et al., "Hydrological Tracers Using Nanobiotechnology: Proof of Concept," Environmental Science and Technology, 46(16):8928-8936, Aug. 21, 2012.

Oxford Gene Technology, "DNA Storage and Quality," Aug. 2011 [retrieved Oct. 30, 2018 https://www.ogt.com/resources/literature/403_dna_storage_and_quality, 5 pages.

European Search Report dated Oct. 20, 2020 issued in Application No. 19738614/-1010/3566046 PCT/US2019013069, 8 pages.

* cited by examiner

DISPENSING SYSTEM FOR APPLYING DNA TAGGANTS USED IN COMBINATIONS TO TAG ARTICLES

FIELD OF THE INVENTION

The present disclosure generally relates to dispensers for DNA taggants and more particularly to apparatus and techniques for applying DNA taggants where distinct combinations of taggants are used to tag information onto an item.

BACKGROUND

Techniques for detecting sequences of DNA are known. In some approaches, a sample is prepared and an analysis process is applied to the sample to cause any DNA in the sample to replicate many times, sufficient for other processes to identify that a particular DNA sequence was present in the sample. For example, if the sample is from a person, the DNA of the sample might be replicated and then the result tested for the presence or lack of presence of a DNA sequence that is unique to a particular person with some probability. In this manner, a sample might be matched to a person, within some probability.

This analysis process is useful for determining whether a particular species is present in a food or agricultural application. For example, there might be a DNA sequence that is unique to a species of nuts and the analysis can replicate the DNA of a sample, including the endogenous DNA of the nuts, sufficient to determine whether or not the sample contained any of those nuts.

In other variations, a DNA sequence that is not endogenous to contents of the sample might be added. For example, synthetic oligonucleotides can be added to a food product to allow that food product to be traced from a source where the oligonucleotides were added to the point at where an analysis is done. The analysis, i.e., sampling, replicating, analyzing would then be able to determine whether or not the food product being tested came from that source. In either case, this requires considerable coordination, as an analysis system would have to be aware of all of the possible synthetic oligonucleotides that are being tested for. If there are, say, thousands of sources, the sampling and analysis for each of those thousand sources can be difficult.

U.S. patent application Ser. No. 14/599,315, published as U.S. Patent Publication 2015/0322426 describes how a set of independent DNA taggants might be used to tag a food product or other item with a bit pattern by having each DNA taggant in the set of independent DNA taggants represent a bit in the bit pattern. Using that approach, $2^N$ unique identifiers can be used and discerned with only N sampling steps needed. In some approaches, the presence of a particular DNA taggant set represents a "1" and the absence of that particular DNA taggant set represents a "0" or the presence of a second particular DNA taggant set represents a "0". Each of the DNA taggants in the taggant set is such that they are biologically inert so as to not interfere with their consumption as part of a food product.

Applying DNA taggant sets can be time-consuming and there is a possibility of cross-contamination where different bit patterns are to be applied in one facility. An improved system for applying DNA taggants used in combinations to tag articles would be beneficial.

SUMMARY

In an improved system for applying DNA taggants used in combinations to tag articles, a plurality of vessels containing distinct DNA taggants are coupled to an application system that provides for mixing of DNA taggants and clearing of those DNA taggants for efficient application of DNA taggants. The selection of a set of DNA taggants can be determined by a computer-controlled system that maps input information to a bit sequence and maps that bit sequence to a particular set of DNA taggants.

Where multiple bit sequences are used in one facility, the system provides for reliably clearing a prior sequence before applying a current sequence. The mapping of information to bit sequences is, in some embodiments, done in consideration of a goal that vessels of DNA taggants are evenly used up, for ease of maintaining the system.

In a specific example, a dispersant system comprises a plurality of taggant vessels, wherein a taggant vessel of the plurality of taggant vessels holds a taggant distinct from other taggants of other taggant vessels of the plurality of taggant vessels, a computer controller, including logic to determine a tag string and convert the tag string into a selection of a taggant set corresponding to selected taggants vessels in the plurality of taggant vessels, a manifold, a plurality of computer-controlled valves, coupled to the computer controller, for allowing or blocking a flow of taggants to the manifold according to the taggant set, a manifold output tube, coupled to the manifold, that outputs a mix of the taggants that flow to form a dispersant formed according to the tag string, and a nozzle for dispersing the dispersant onto an object to be tagged.

The taggant can comprise a DNA taggant, such as a DNA taggant comprising a static portion that is present in each of the taggants in the plurality of taggant vessels and a dynamic portion that is unique such that a first taggant from a first taggant vessel is distinguishable from a second taggant from a second taggant vessel. The taggants in the taggant vessels might be mixed with ethanol as a carrier of the taggants. A nozzle structure might provide for mixing of the dispersant with an atomizing air stream.

The computer controller might include logic for, and handle, flushing at least the manifold output tube and the nozzle between changes in the tag string from a first tag string to a second tag string. Each of the taggant vessels might correspond to a position in the tag string and the computer controller might include logic to allow for flow of a first taggant when a character at the position in the tag string that corresponds to the first taggant is a first value and to block flow of the first taggant when the character at the position in the tag string that corresponds to the first taggant is a second value. Example values are "1" and "0".

The computer controller might include logic to select a first tag string for a first lot of one or more first objects to be tagged with the first tag string and select a second tag string for a second lot of one or more second objects to be tagged with the second tag string, wherein the first tag string and the second tag string have a low Hamming distance. Selection of tag strings for distinct lots of one or more objects to be tagged might be such that the "1" characters and "0" characters for each string position might occur at approximately the same rate, so that consumption of taggants evens out over the plurality of taggant vessels. The tag strings might include redundancy usable for error correction.

The following detailed description together with the accompanying drawings will provide a better understanding of the nature and advantages of the present invention.

BRIEF DESCRIPTION OF THE DRAWINGS

Various embodiments in accordance with the present disclosure will be described with reference to the drawings, in which.

DETAILED DESCRIPTION

Figure 1:
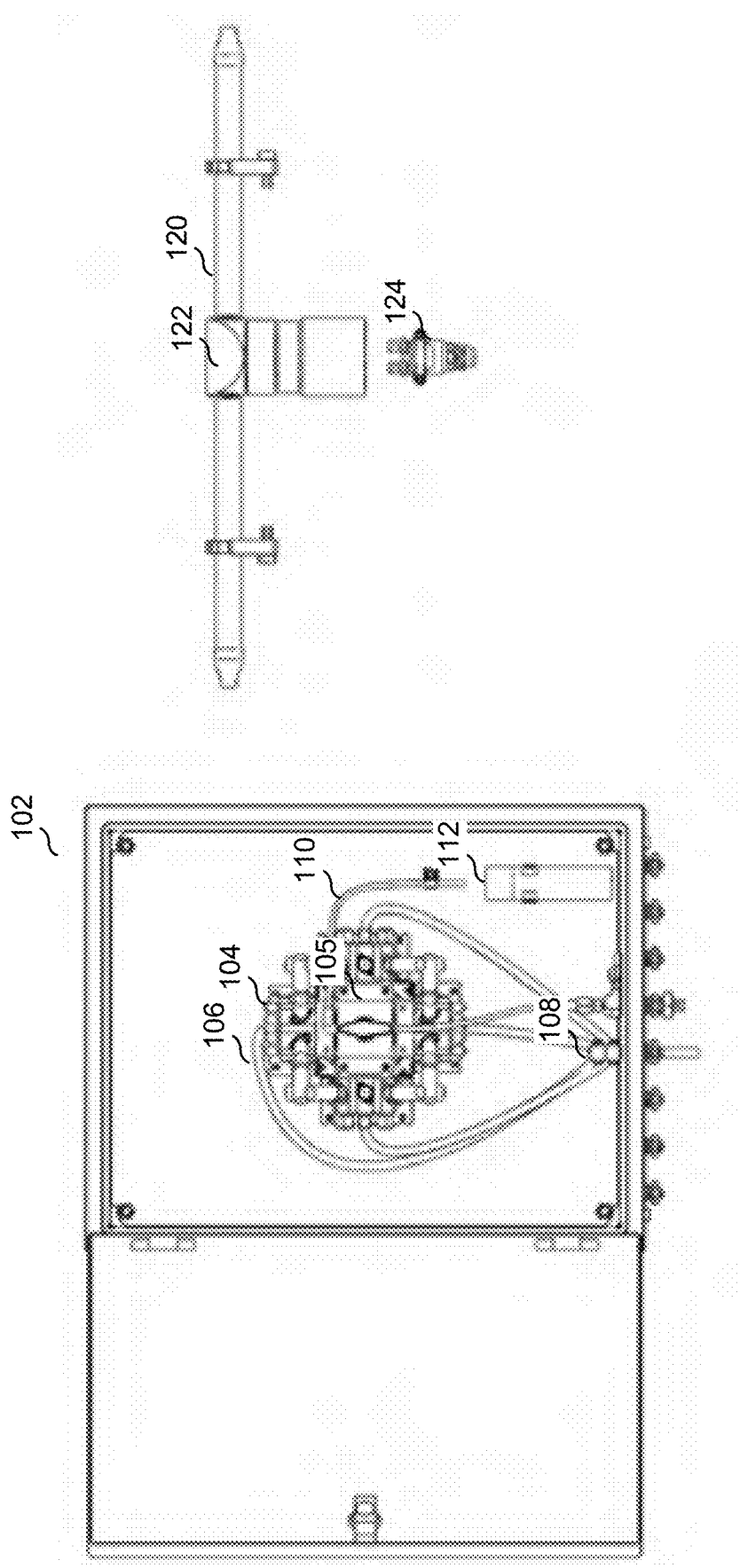
FIG. 1 illustrates a dispensing system that applies DNA taggants that has multiple spray manifolds.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Techniques described and suggested herein include methods and apparatus for the application of DNA taggants that correspond to encoded information that can be applied to objects, including food items, in a manner that allows for later reading of this encoded information from the objects. In a specific embodiment, the DNA taggants are unique, each taggant represents a bit position and the pattern of presence or absence of one of the DNA taggants corresponds to a bit value of 1 or 0 and the pattern of DNA taggants that are present or absent forms a binary number representing the encoded information. In another embodiment, the presence of a first DNA taggant is used to signal a value of "1" of the encoded information and the presence of a second DNA taggant is used to signal a value of "0" of the encoded information. The apparatus that adds the DNA taggants to the objects can be configured such that the encoded information can change from object to object and not cross-contaminate objects with DNA taggants that are for one object but not another.

In a specific example, there is a set of 32 DNA taggants to work with and so there are $2^{32}$ possible combinations of DNA taggants that can be applied to an object, thus encoding the object with a 32-bit value corresponding to a specific "tag string" that might be represented by a sequence of 32 binary values each having a bit location in the tag string. It should be understood that other numbers are also possible and in the general case, a tag string might be represented as an indexed array of values, each having an index or position in the tag string, where the values might be binary values.

For example, it might be that 28 bits (and 28 DNA taggants) would be sufficient for a particular application. For example, if there are 128 producers of apples, each having 8 facilities, and they group their apples by lot such that they output 256 lots per year, one per day, over the course of 16 years, the manufacturer, facility, lot, and year can be encoded in a 7+3+8+4=22 bit tag string and so 22 bits and 22 DNA taggants are sufficient and that leaves room for checksum bits/taggants to be added. In this simplified example, the number of possible values for each of the variables is a power of two, but that is not required and other values can be used. Conventional mapping of values to tag strings can be done.

As used herein, a DNA taggant is a material that includes an oligonucleotide and possibly other material. In a specific example, each DNA taggant comprises a static part and an identifier part, wherein all of the DNA taggants have the same static part and thus it can be used to differentiate between the set of DNA taggants in use and other DNA that might be present in a sample. Preferably, the presence of a DNA taggant can be done even when there are very low concentrations of the DNA taggant in or on the object. Thus, where there is a dispersant expected to be found in the sample, the sample and/or the dispersant thereon is sampled, detected, error-corrected as needed, etc. to determine the tag string that was applied to the object.

A tag string has an associated DNA taggant set, which is a selection of particular DNA taggants used, or to be used, on an object to "label" that object with the tag string. The object might be an item being sold, bulk material, packaging, or other physical object or item where labeling according to the tag string is useful. In particular, where a printed label is not workable or viable, applying the tag string could be done instead. For illustration purposes, consider the case where the tag string comprises binary values each having a bit position in the string, such as "01101001 10101001 10100111 10010101" which has a "0" in the first bit position, "1" in the second and third bit positions, and "1" in the $32^{nd}$ bit position. A specific DNA taggant is associated with each bit position of the tag string and labeling an object might comprise determining which bit positions of the tag string are "1", determining which DNA taggants go with those bit positions, and applying those DNA taggants (referred to herein as a "taggant set") to the object, and not applying the DNA taggants that go with the bit positions of the tag string that have "0" values.

The tag string could represent different information. For example, in a particular industry or application, some of the bit positions might correspond to the company name, others to a serial number, others to a production date or location, etc. By later sampling the object on which the taggant set was applied, a tag detecting system can decode the taggant set and from there determine the tag string that was applied to the object.

In some embodiments, all or part of the tag string is an index value that points to a record in an external database that provides data about that particular record. In those embodiments, the tag string assigned to an object might be entirely arbitrary and an external database of object information would be used to get data about the object rather than decoding any data about the object from the bit pattern itself.

In an example distribution system, there are lots and each lot has applied to it a specific tag string and a first lot receives a first taggant set corresponding to a first tag string and then a second lot receives a second taggant set corresponding to a second tag string different than the first lot. The first lot might be multiple items, such as a plurality of melons, or the first lot might be a single item, such as a bag of coffee beans. In the case of a bag, the distribution system might be integrated in with an automated bag filling line. In such a line, a new bag is positioned in the system and is clamped to the filling line chute to receive product. Perhaps before the first bag is in place, the distribution system initially dispenses plain carrier (no taggants) in the "dead volume" (the volume of the piping beyond actuating valves). Then when the empty bag is in place, or after the bag is filled, but before it is declamped and stitched closed, the distribution system actuates certain valves of the distribution system to push out the plain carrier and then push out specific taggants based on that bag's designated tag string. It may be that delivery is timed so that the plain carrier residing in the dead volume is delivered during clamping to the bottom of the empty bag and the taggants are delivered as the product is filling the bag. Perhaps the taggant valves are de-energized before the bag is full but the plain carrier valve remains energized, so that at the completion of the bag filing cycle the dead volume has been filled by plain carrier at which point the plain carrier valve is de-energized. The cycle repeats with a new taggant combination for the second bag and so on with the plain carrier effectively flushing the lines so that only the desired taggants appear for a given lot.

Instead of a spray, the carrier/taggants might be applied by immersion.

The carrier can be liquid or solid or in between, as might be the taggants. The taggants might be naked DNA or DNA included in a matrix, such as a carnauba wax coating, as is often used for various types of fresh fruit, or if the carrier is a volatile liquid such as ethanol, water, etc., the taggant remains in direct contact with the product. Studies have shown that its stability is limited and generally shorter than the product shelf life relative to being included in some persistent matrix.

In a solid form such as a powder, the taggant might have been previously encapsulated in a solid carrier (such as maltodextrin, gelatin, etc.), which can provide superior stability that is usually in excess of one or two years. The solid form is a convenient form for application of taggants to dry and granular products such as flour, sugar, etc. Taggants encapsulated in solid matrixes can also be used in processed foods and liquids (e.g., juices, oils, etc.) preferably encapsulated in a solid matrix that does not dissolve in the product, as that would release the DNA of the taggant and may limit its stability.

For commodities such as fertilizers, beans, grains, etc., application of taggants in solid form (encapsulated) might be preferred due to stability considerations. However, for high speed processes, as when, for example, a taggant must be uniformly applied to product during the bag filling process (which might be a 2-4 second cycle), liquid carriers might be preferred as powder can be very difficult to manage at those speeds and prone to cross contamination. A cost effective method to apply a taggant in solid form is as very fine powder, which increases the number of taggant particles per volume of product. This increases the probability that the taggant will be recovered from a small sample of product when the product is tested for the presence of the taggants. However, when fine particles are used, they may remain airborne for minutes or even hours, possibly migrating to lots where they were not intended to be applied, which would cause identification errors when taggant reading is done on a sample of the product. Loose particles also might cause cross-lot contamination at the point of testing as the product is taken out of a bag. In these situations, application of the taggants in a liquid form would simplify the application process but might result in diminished stability.

In an improved application process, a hybrid method is used that combines the ease of the liquid application with the stability of the solid carriers. In this approach, the taggant is encapsulated in powder granules that are suspended in a liquid in which the granules do not dissolve. Examples of encapsulating carriers include gelatins, agarose gel, carra- geenan powder, etc. and the liquid carrier might be ethanol. Another example is ethyl cellulose powder as the encapsulating carrier and water as the liquid carrier. The distribution system can then spray a product or immerse the product, thus improving uniform application and reducing the potential for loose powder and resulting cross contamination. The amount of liquid carrier required is usually very small (in one example, less than 50 mL per 50 kg bag). The liquid carrier either evaporates or is absorbed by the product leaving the taggant as an encapsulated powder in the sealed bag.

In addition, use of gels promotes adhesion of the powders to the product, reducing the risk of contamination due to loose powder when the bag is opened. Other adhesives may be added to the liquid to promote adhesion. For example, applying ethyl cellulose powder suspended in a 0.5% agar-agar solution will create a film containing ethyl cellulose DNA tagged powder on the surface of the product.

A dispensing system might include tanks or vessels that contain one of the DNA taggants (or taggants in encapsulating carriers) in suspension, powder, or other forms such as emulsions, liposomes in liquid, or coacervations (a type of electrostatically-driven liquid-liquid phase separation, such as spherical aggregates of colloidal droplets held together by hydrophobic force measuring from 1 to 100 micrometers across or some other diameter, while their soluble precursors are typically on the order of less than 200 nm or some other distance). A computer control system might control the dispensing of specific patterns of the DNA taggants. The taggant vessels have a finite volume and so DNA taggant gets consumed. By careful selection of which patterns are used, the consumption can be controlled so that the taggant vessels do not need to be filled at inconvenient times.

The dispensing system might be required to deliver distinct taggant sets (thus marking distinct objects or lots with different tag strings) at very high speed, as many as 20-25 per minute or more. In an implementation, a computer processor determines what tag string is to be applied and then sends electrical signals and commands to various modules, ultimately resulting in the desired taggant set being added or applied to the object being marked. It may be that each object marked gets a different taggant set, so the dispensing system would carefully control the distribution of taggants so that the taggants of the taggant set applied to a current object do not get used during application of a next object (unless those are taggants that are part of the taggant set for both the current object and the next object).

FIG. 1 illustrates a dispensing system 102 that applies DNA taggants that has multiple distribution manifolds 104. As shown there, each distribution manifold 104 is mounted on a face of a mounting post 105. By compactly mounting the distribution manifolds 104, the amount of dead volume between where the DNA taggants are introduced and mixed and where they are sprayed out is reduced. In this specific embodiment, DNA taggants are selected at a distribution manifold 104 and the material that passes through each manifold is combined at a shot manifold 108. A diversion line 110 is provided to divert the dispensate (i.e., the material to be dispensed, comprising taggant, encapsulated or not, and a carrier) to a vial 112 for testing and other purposes.

Each of the distribution manifolds are supplied by eight lines in this example (not shown) and output lines 106 from each distribution manifold 104 runs to shot manifold 108 as shown, using lines such as output line 106. From the eight supply lines to a distribution manifold, some combination of those supplies is mixed at the distribution manifold and output in output line 106. The combination is determined by which valves on which of the supply lines are to be used.

The dispensing system might dispense a dispensate that is a liquid suspension, a dry material, or a powder with a fast evaporating carrier, such as ethanol. The dispensing system involves manifolds that are supplied by the individual taggants and possibly a carrier. A carrier might be a liquid carrier. The dispensing system might also distribute the carrier without any taggants, perhaps when needed to flush certain supply lines.

As illustrated, the dispensate is distributed via a support 120 mounted inside a filling line chute where products are filled into containers, for example. The supports 120 support a nozzle 124 and a shroud 122 so that the nozzle 124 can be suspended above a filling line chute or inside the filing line chute, suspended above the bag. The supports 120 have hollow centers, such that one serves as a conduit for a liquid supply and the other for atomizing air line in one example. With this approach, the dispensate is provided to the shroud 122 and from nozzle 124, and the dispensate is applied to the product.

Figure 2:
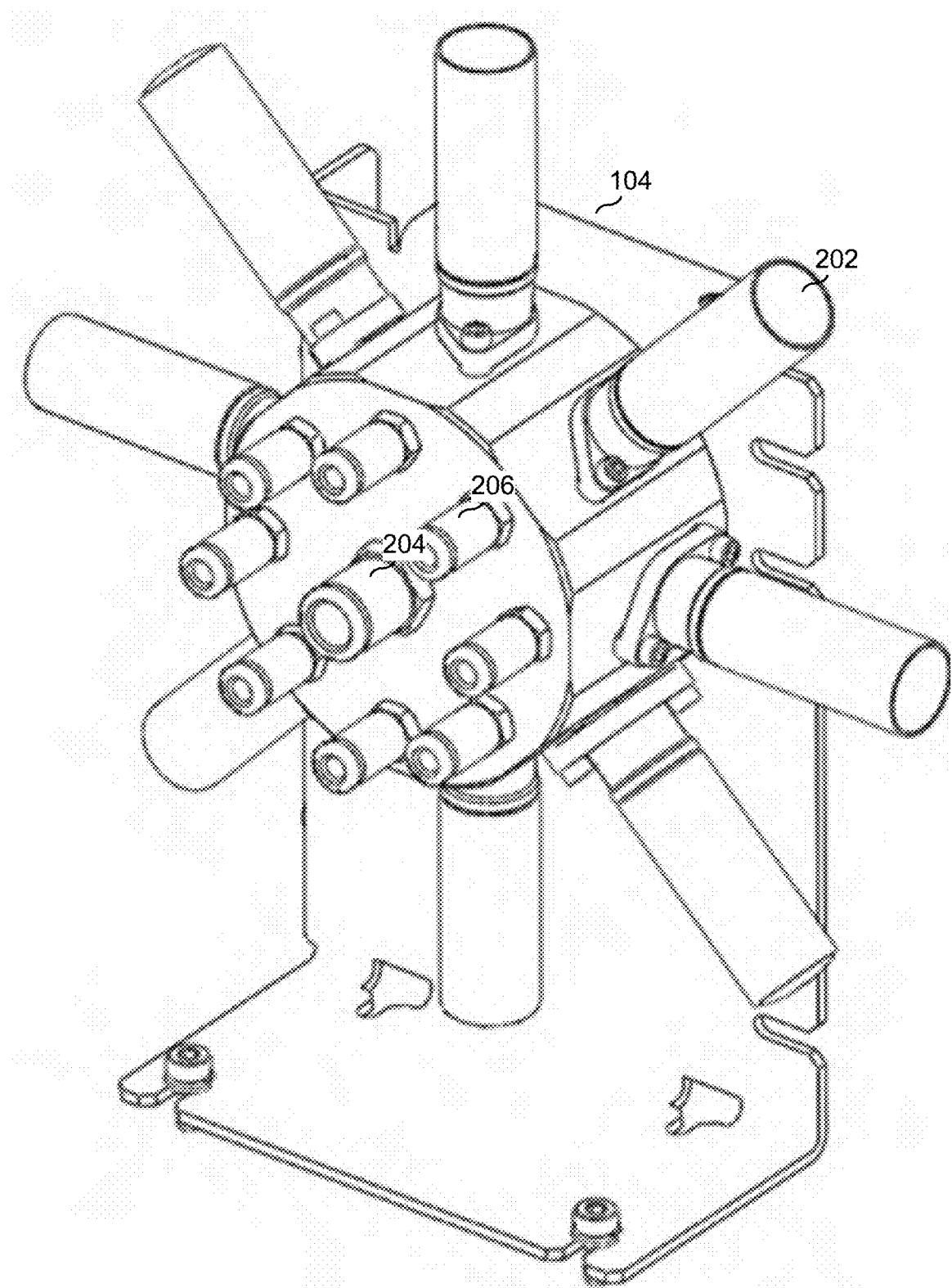
FIG. 2 illustrates spray manifold in greater detail.

FIG. 2 illustrates one distribution manifold 104 in greater detail, including solenoid valves 202, an output port 204 (which is in turn is connected to an output line 106 illustrated in FIG. 1), and input ports 206 (one per solenoid valve 202). The taggants from each tank come into input ports 206. The combined dispensate goes out through output port 204. Under computer control, solenoid valves 202 either allow a corresponding taggant component from a corresponding input port 206 to flow to output port 204 or block the corresponding taggant component from flowing to output port 204. As explained herein, when changing from one bit pattern to another bit pattern, the system is flushed with carrier or otherwise in order to remove any remaining taggant component before changing to a new taggant set.

FIG. 2 illustrates one distribution manifold. FIG. 1 illustrates the mounting of four distribution manifolds on a support post. As used herein, the number of distribution manifolds used is represented by M, and in FIG. 1, M=4. Other values for M are possible, such as three, eight or some other number. Distribution manifold 104 shown in FIG. 2 is shown with eight solenoid valves. As used herein, the number of solenoid valves per manifold used is represented by N, and in FIG. 1, N=8. Other values for N are possible, such as four, seven, ten, sixteen or some other number.

The inner volume of the piping and spray nozzles is an important consideration. As the distribution system switches lots and changes the tag string to be applied, this would mean that a different taggant set is applied. Preferably, the inner volume does not contain taggants from a prior lot when applying taggant to a current lot when the prior lot's taggant set included a taggant that is not in the current lot's taggant set. This can be dealt with by using plain carrier for a time and thus flushing all the lines. The dispensing system might be required to deliver distinct taggant sets that change as often as every three to five seconds and thus flushing should happen quickly and reliably. The dispensing system controls the flow of taggant and carriers (powders, liquids, gasses, etc.) via solenoid valves 202. A computer control system can control the positioning of various components, the opening/closing of valves, the sensing of state (mechanical state, chemical contents, temperature, volume of material available, etc.) and processing to act on that information as programmed.

Figure 3:
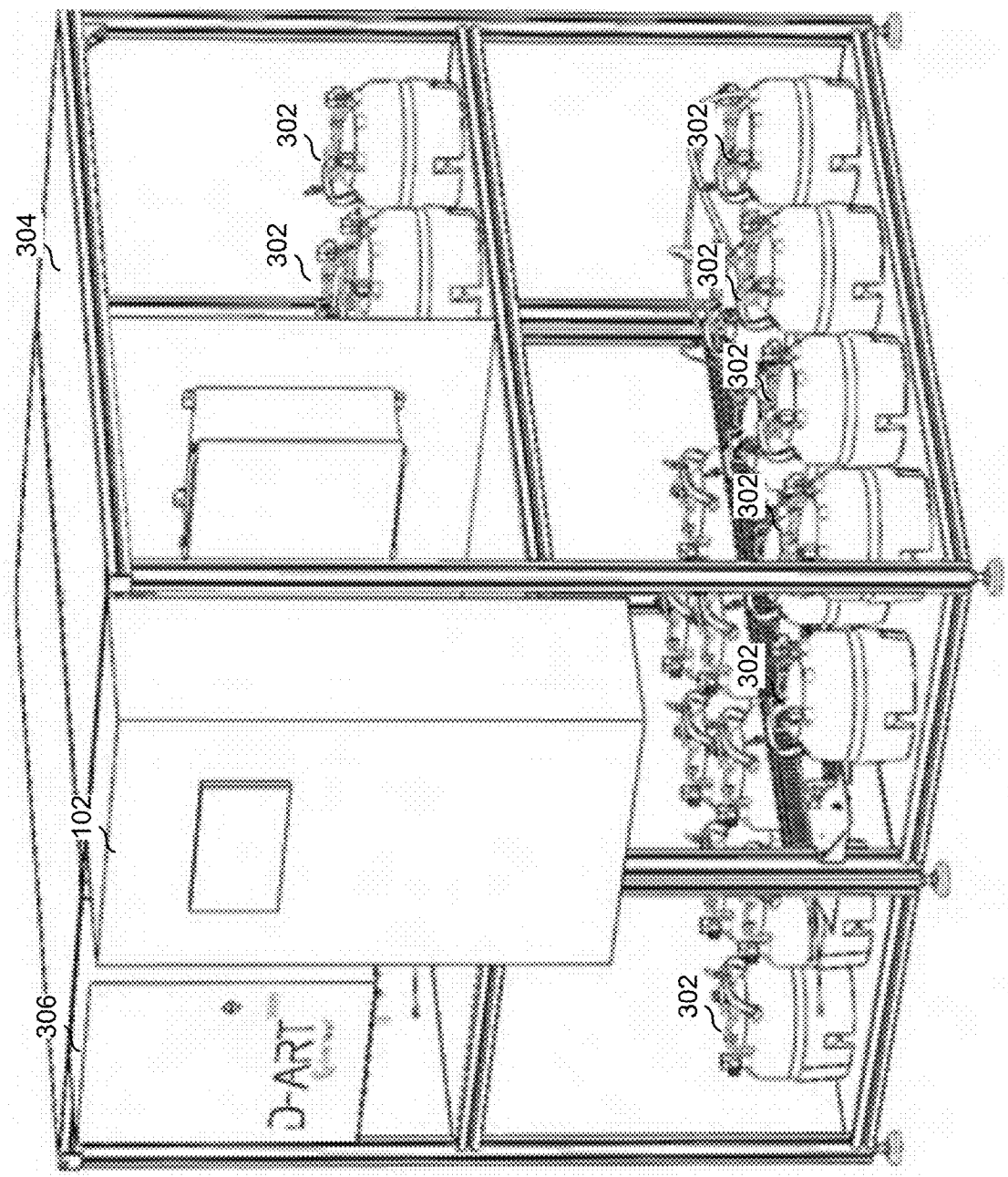
FIG. 3 illustrates shelving for holding taggant vessels and a distribution manifold.

FIG. 3 illustrates taggant vessels 302 and shelving 304 that also supports a distribution manifold 104. A manifold might be supplied with compressed air and a pure liquid carrier stream (no taggants) that are used to supply the taggant tanks. The volume between the spray manifolds (shown in FIG. 1) where the taggants become mixed and the nozzle is the dead volume of the system that may need to get flushed each time. To reduce the need to refill vessels and waste, it might be desirable to keep the dead volume to a minimum. This dead volume might be reduced by careful positioning of the mixing manifold close to the nozzle and the use of components with small internal volume to minimize the dead volume. Tubing (not shown) connects the vessels to the corresponding solenoid valves on the manifolds (one of which is shown in detail in FIG. 2). Then the valves are actuated as needed to produce the desired combination. The four manifolds of FIG. 1 supply a shot manifold that combines the streams and supplies them to the nozzle 124. Also shown are electrical signal and/or computer control cables that connect a computer control unit 306 to the distribution manifold 104. In other embodiments, the computer control unit 306 is more distant from the distribution manifold 104.

Figure 4:
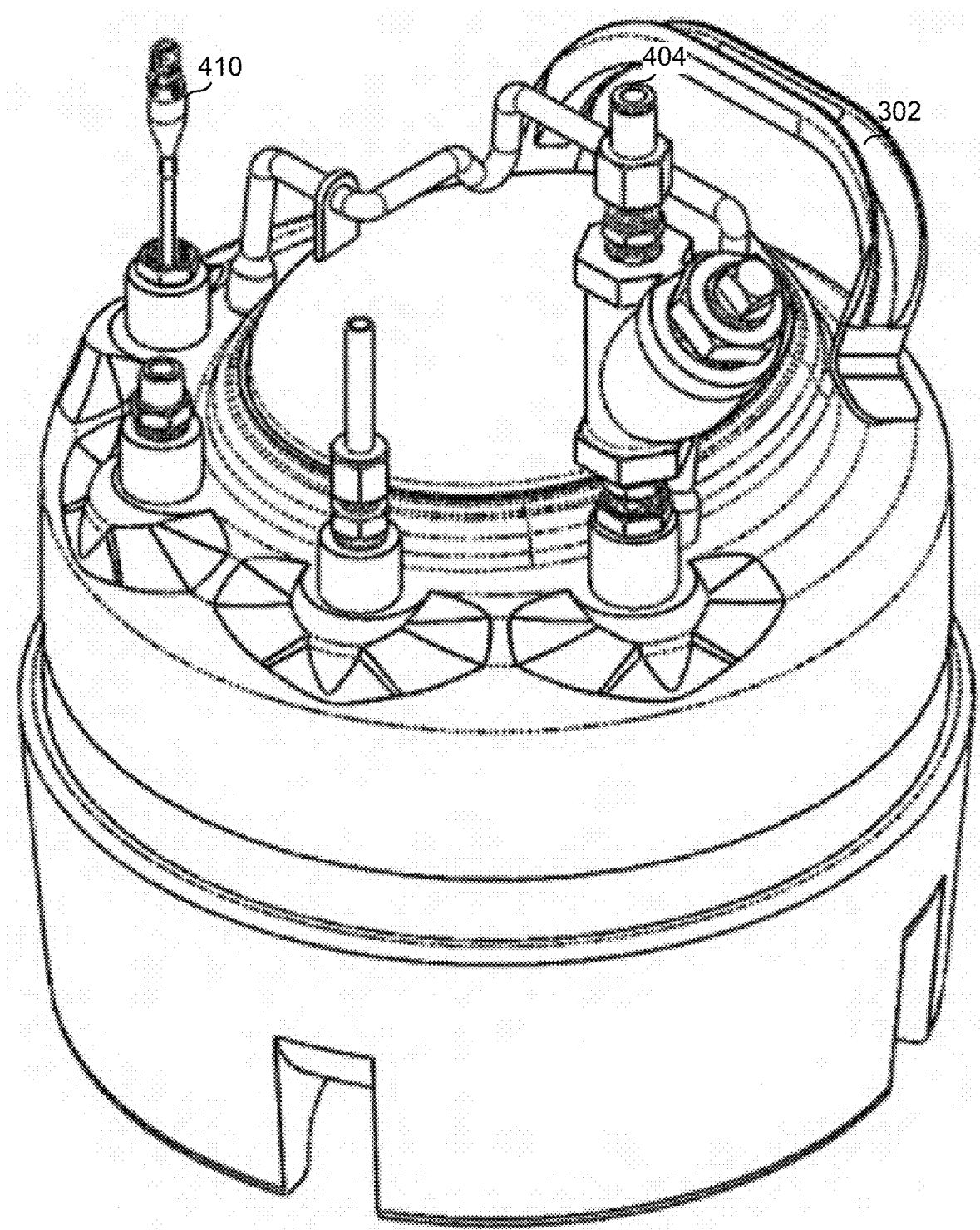
FIG. 4 illustrates the vessel of FIG. 3 in more detail.

FIG. 4 illustrates the taggant vessel 302 in more detail. As shown there, the taggant vessel 302 includes a valve 404 and a sensor I/O connector 410. One of the inputs shown might be used to supply compressed air to pressurize the vessel and a dip tube that draws the solution to the manifold. A port might be available for a concentric fitting used with an external pump to keep the taggant solution stirred. A level sensor is provided, and a number of other sensors can be installed.

Figure 5:
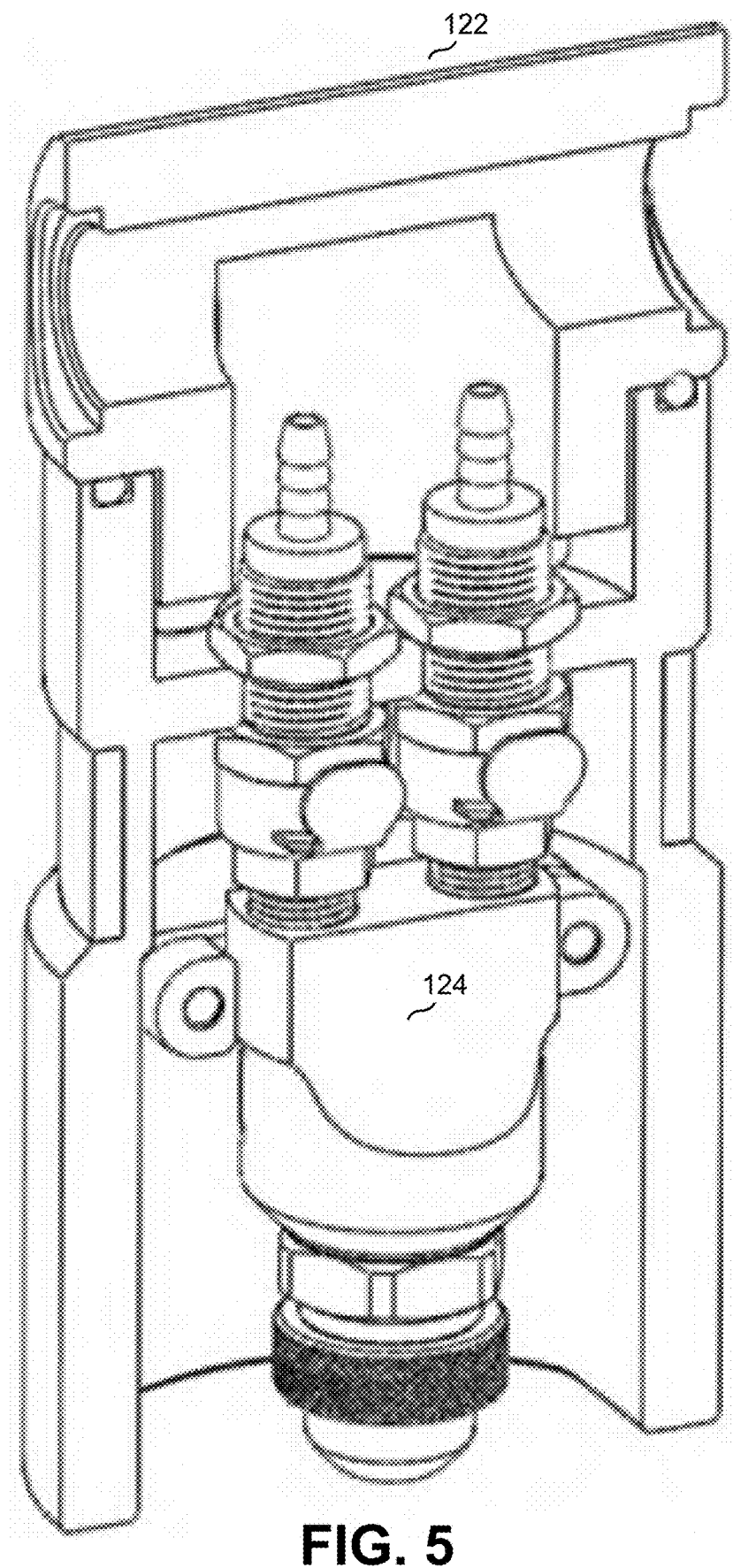
FIG. 5 illustrates the nozzle and shroud of FIG. 1 in more detail.

FIG. 5 illustrates the nozzle 124 and shroud 122 in more detail. This would be downstream of the distribution manifolds 104. Quick connects can be used for easy removal of the nozzle for servicing. Using rubber fittings allows the nozzle to be easily released. The two connections are the taggant solutions and atomizing air, which might arrive by tubing (see FIG. 6) inside the supports.

Figure 6:
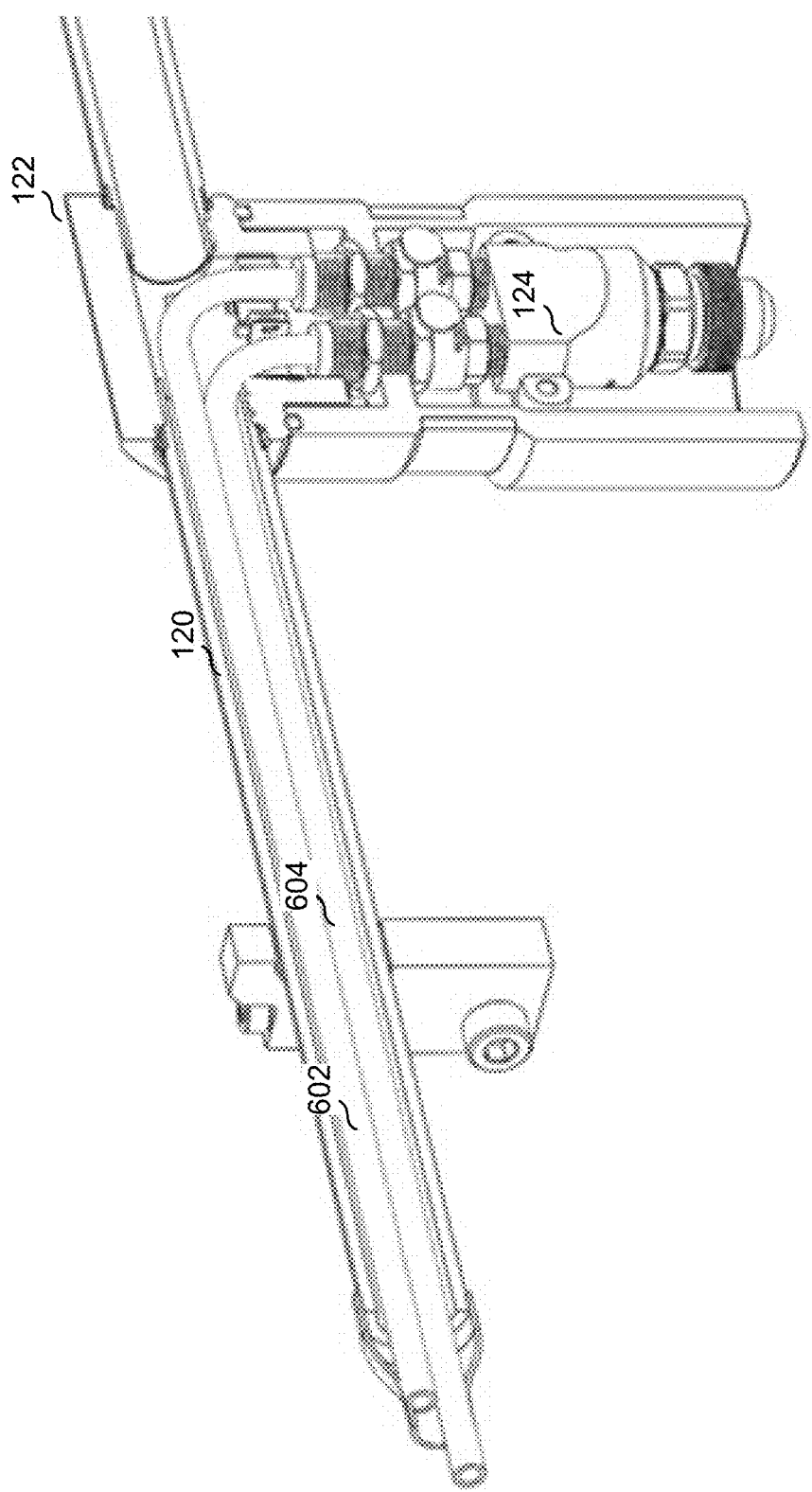
FIG. 6 illustrates supply lines to the nozzle of FIG. 5.

FIG. 6 illustrates supply lines to the nozzle of FIG. 5. As shown there, a solvent/dispersant supply line 602 is provided to nozzle 124 via support 120, as well as a taggant supply line 604. The solvent/dispersant supply line 602 might supply water, ethanol, atomizing air, or another component that would support the dispersing of taggants. The taggant supply line 604 might supply the taggant supported by ethanol, water, or as a powder or other form. In a specific example, the solvent/dispersant supply line 602 provides pressurized air and the taggant supply line 604 provides taggant that was mixed with ethanol at the taggant vessel. The taggant present in the taggant supply line 604 would be a combination of taggants that is determined by what solenoids were activated at the manifolds and combined there. When switching from one set of taggants to another set of taggants, taggant supply line 604 might contain only ethanol or other carrier without taggants. Under computer control, the flushing might occur between bags, packaging, or objects being below nozzle 124, and might just evaporate after being sprayed. By using a narrow diameter for the taggant supply line 604, and suitable location relative to the manifolds, the amount of dead volume needed to flush can be kept to a minimum. The solvent/dispersant supply line 602 and the taggant supply line 604 can be easily detached from nozzle 124 for easy cleaning.

In a production line where product is to be tagged with taggant sets the thus imbuing the product with a readable tag string, the dispersant system might be located where bags of product are filled. At that location, there might be shelving for a plurality of taggant vessels as shown in FIG. 3 and FIG. 4, with the vessels having openings for filling taggant material therein and for providing a carrier such as ethanol, if needed, and tubing from the taggant vessels to the manifolds such as is shown in FIG. 2. Under computer control, solenoid valves let a selected set of taggants pass and be combined in the manifolds, such as shown in FIG. 1. The combined taggants are then provided to a nozzle in combination with a solvent/dispersant as illustrated in FIG. 6, as the process is laid out in FIG. 7.

The taggants might originate as a powder used to fill taggant vessels that are then filled with a solvent and mixed to form the dispensate. Where the solvent is ethanol, the ethanol might evaporate in due course, perhaps after a bag has been filled and tagged, in which case the taggant might adhere to the product that is tagged, but once dried might distribute throughout the bag as the closed bag is further processed. This would have advantages. For example, suppose a filling line processes 15 bags per minute and each has a different tag string to be associated with the contents of the bag. The distribution system might spray aerosolized dispensate into a bag being filled with granular product when the bag is one quarter full, where the aerosolized dispensate might be DNA taggants as a powder suspended in ethanol and mixed with pressurized air to spray out of a nozzle into the filling bag. Then, there might be another spray when the bag is half full and then before sealing the bag, the distribution system can begin a flushing of the lines so that the taggant set for a given bag is fully out by the time the bag is sealed and can start on the taggant set for the next bag without needing to slow down the filling process.

Where the taggant is a powder suspended in an evaporating solvent, during further processing of the sealed bags, the taggant could become more evenly distributed so that a sample from any part of the bag can be used to reveal the taggant set (and thus the tag string) used for that bag. The amount of solvent might be selected to be low enough to evaporate, but not so low that it is hard to flow the taggant through the tubing and not so low that it evaporates while the product is still filling the bag, as that might result in some of the dried taggant becoming airborne and cross-contaminating other bags, which can be an issue where tag strings are changing often. In this manner, taggant is easily transported, tubing and lines are easily flushed, and the taggant reverts to a dry powder form, but not too soon.

Where the product being marked is a liquid, the mixing and evaporation is less of a concern. In either case, very small quantities of taggant can be used and still detected when sampled.

Figure 7:
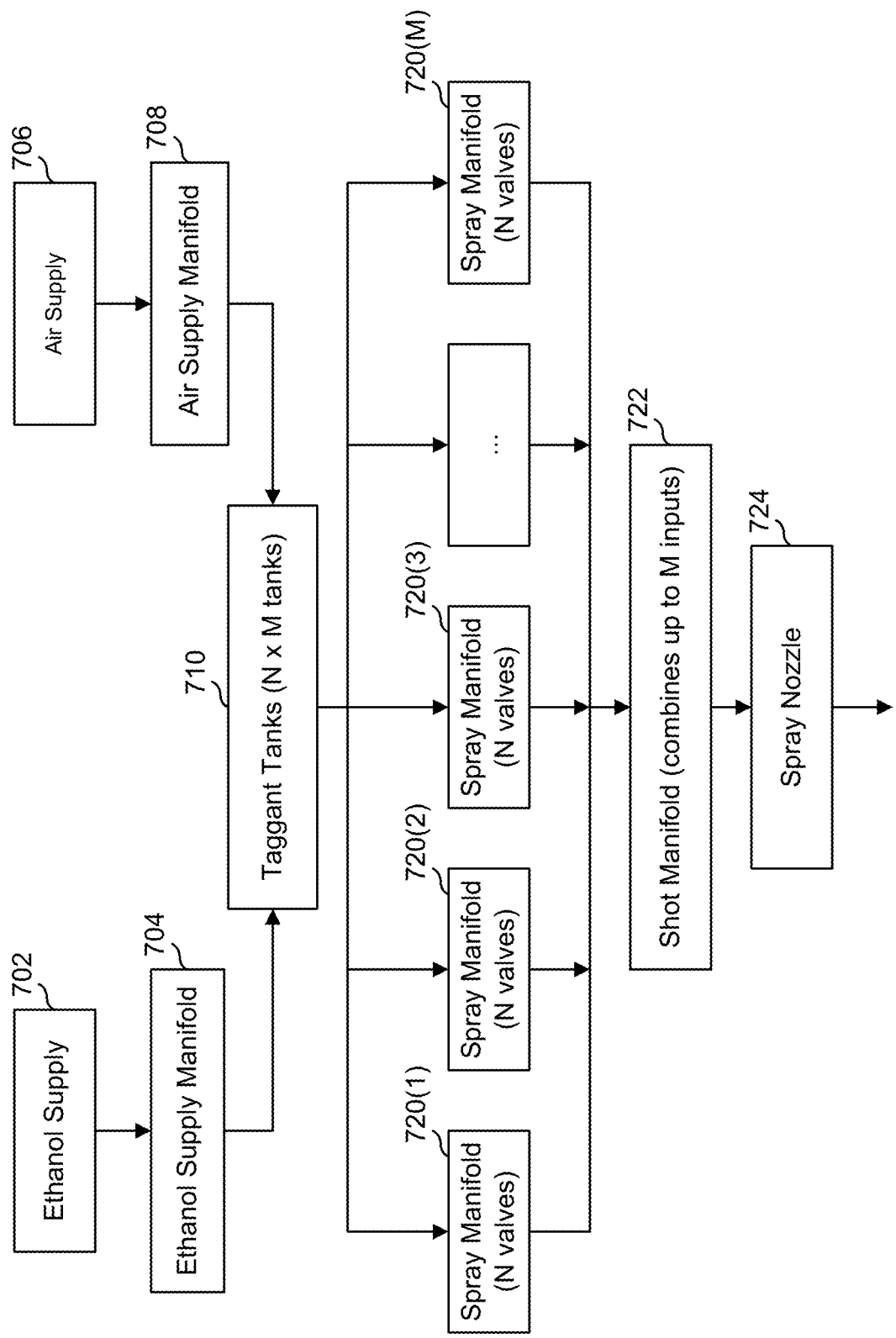
FIG. 7 illustrates a logical arrangement of components of the distribution system, wherein each box represents a container, dispenser or conduit, and the arrows indicate where controlled flows can occur.

FIG. 7 illustrates a logical arrangement of components of the distribution system, wherein each box represents a container, dispenser or conduit, and the arrows indicate where controlled flows can occur. As shown there, ethanol can be supplied from an ethanol supply tank 702 via a manifold 704 and water can be supplied from a water tank 706 via a manifold 708. These liquid carriers can be supplied to taggant tanks 710.

Under the computer control, contents of the taggant tanks 710 are supplied to spray manifolds 720 and those provide the dispensate to a shot manifold 722 then to a spray nozzle 724. In a specific implementation, there is a pure ethanol supply and a compressed air supply. A fresh vessel is loaded with DNA taggant, such as from a pouch in the form of powder. The vessels are then filled with ethanol and the mixing pumps are turned on to mix the suspension. The vessels are closed and pressurized with compressed air. Each vessel is connected via a tube to an input of a manifold controlled by a solenoid valve (see FIG. 2) on one of the manifolds (see FIG. 1). The control system actuates the required valves to produce a given combination of taggants that form a taggant set. What comes out of the manifolds goes into a shot manifold (that combines material from other manifolds) and from there into the nozzle. The whole system is pressurized and an additional compressed air line at the nozzle helps atomize the liquid dispensate.

To reduce taggant carry-over from lot to lot, a particular sequence might be used for tag strings (and thus taggant sets). A desirable sequence of taggant sets might have a property such that, as between a first taggant set used on one lot and a second taggant set used on a second lot that follows the first lot, the number of taggants that change from the first taggant set to the second taggant set is a low number. For example, if a current tag string and a next tag string differ by only one bit, i.e., one taggant is present in one of the taggant sets and absent in the other taggant set, and all the other taggants are the same, that number would be one. In that instance, there are reduced opportunities for deleterious cross-contamination. A Gray Code is a known code that provides sequential patterns that have this property. An advantage in the present distribution system is that even if there is some cross-contamination and as a result one of the bits of the pattern is read in error, it may well be that a tested product is deemed to be in a lot other than its original lot, but that other lot may well be one that is close in time to the original lot.

Another desirable property is that, where the binary bit "1" corresponds to the use of a taggant and "0" corresponds to the nonuse of that taggant, the number of "1" that occur over all bit patterns is about the same. If that is the case, then the taggant vessels would tend to be used up evenly which can be logistically better than having some taggants run out sooner than others.

In a specific implementation, the computer processor selects a start number from among 32-bit numbers and uses that as the first tag string. The processor directs the distribution system to apply to the first lot of product the taggant set that corresponds to that tag string. For the second lot, the processor selects a random number between 0 and 31 (call it k) and the second tag string is the first tag string with its k-th bit flipped. For subsequent lots, a similar process is done, but the processor maintains a list of the already used tag strings and selects a different value fork if flipping the bit for the selected value fork would result in an already used tag string. If there are no such tag strings remaining (i.e., if all 32 numbers within a Hamming distance of 1 from the current tag string have already been used), then the processor might select another tag string that has not been used but has a low Hamming distance from the current tag string. In other variations, k is not selected randomly, but according to a rule that results in, at least approximately, the same number of "1"s appearing in each bit location.

In some implementations, the bit patterns include error correction. For example, error correcting codes might be used where there are 27 data bits and 5 redundant bits. In a general case, there are n different taggants and $2^k$ different possible taggant sets, so there would be n-k redundant bits and k information bits. This would allow for possibly correcting for n-k erasures or around (n-k)/2 errors. Errors might occur where an intended taggant is found on an object and erasures might occur where the testing and processing of a sample reveals an ambiguity as to whether or not a taggant was present.

According to one embodiment, the techniques described herein are implemented by one or generalized computing systems programmed to perform the techniques pursuant to program instructions in firmware, memory, other storage, or a combination. Special-purpose computing devices may be used, such as desktop computer systems, portable computer systems, handheld devices, networking devices or any other device that incorporates hard-wired and/or program logic to implement the techniques.

Figure 8:
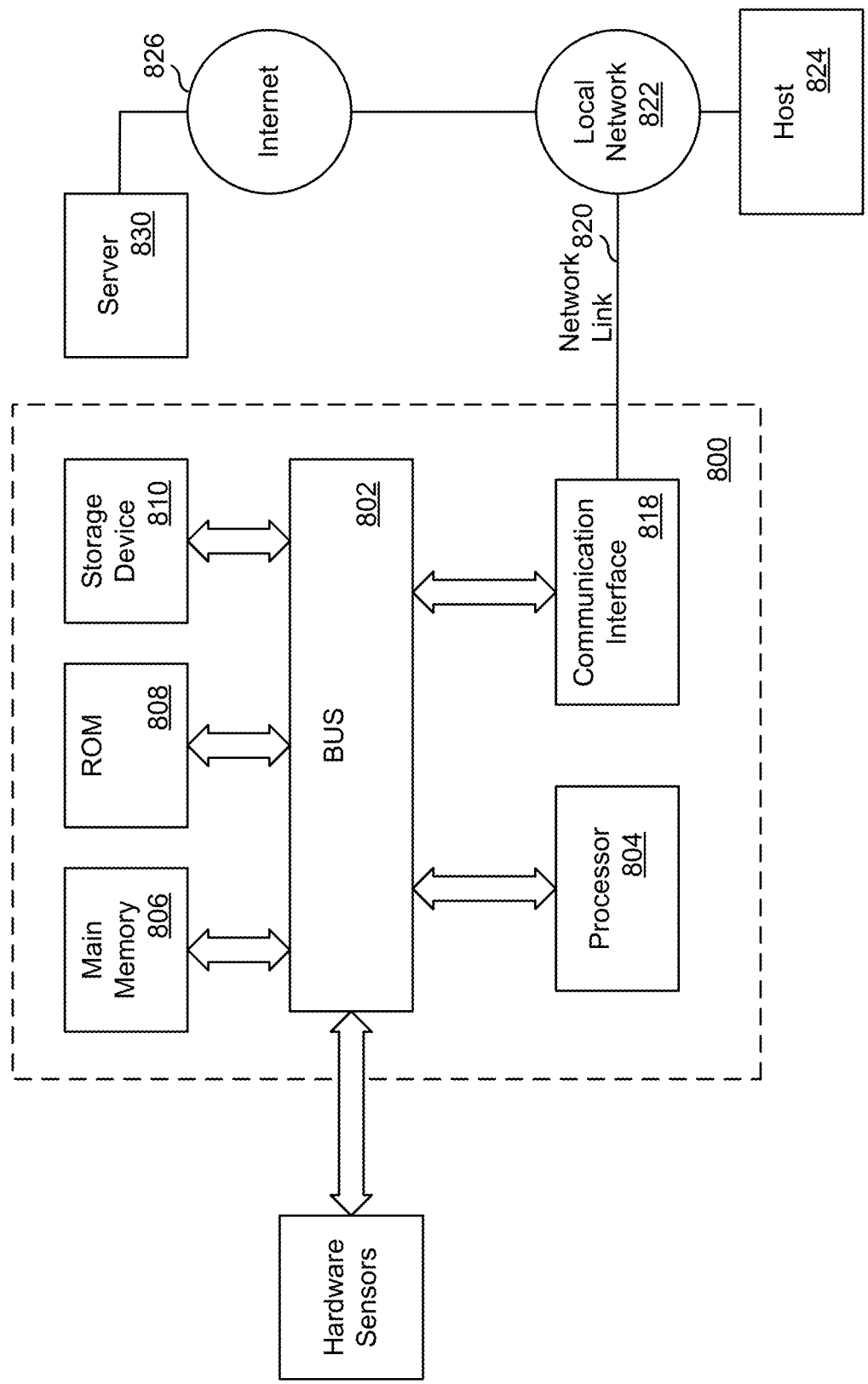
FIG. 8 is a block diagram that illustrates a computer system upon which an embodiment of the invention may be implemented.

For example, FIG. 8 is a block diagram that illustrates a computer system 800 upon which an embodiment of the invention may be implemented. Computer system 800 includes a bus 802 or other communication mechanism for communicating information, and a processor 804 coupled with bus 802 for processing information. Processor 804 may be, for example, a general purpose microprocessor.

Computer system 800 also includes a main memory 806, such as a random access memory (RAM) or other dynamic storage device, coupled to bus 802 for storing information and instructions to be executed by processor 804. Main memory 806 also may be used for storing temporary variables or other intermediate information during execution of instructions to be executed by processor 804. Such instructions, when stored in non-transitory storage media accessible to processor 804, render computer system 800 into a special-purpose machine that is customized to perform the operations specified in the instructions.

Computer system 800 further includes a read only memory (ROM) 808 or other static storage device coupled to bus 802 for storing static information and instructions for processor 804. A storage device 810, such as a magnetic disk or optical disk, is provided and coupled to bus 802 for storing information and instructions.

Computer system 800 may be coupled via bus 802 to a display 812, such as a computer monitor, for displaying information to a computer user. An input device 814, including alphanumeric and other keys, is coupled to bus 802 for communicating information and command selections to processor 804. Another type of user input device is cursor control 816, such as a mouse, a trackball, or cursor direction keys for communicating direction information and command selections to processor 804 and for controlling cursor movement on display 812. This input device typically has two degrees of freedom in two axes, a first axis (e.g., x) and a second axis (e.g., y), that allows the device to specify positions in a plane.

Computer system 800 may implement the techniques described herein using customized hard-wired logic, one or more ASICs or FPGAs, firmware and/or program logic which in combination with the computer system causes or programs computer system 800 to be a special-purpose machine. According to one embodiment, the techniques herein are performed by computer system 800 in response to processor 804 executing one or more sequences of one or more instructions contained in main memory 806. Such instructions may be read into main memory 806 from another storage medium, such as storage device 810. Execution of the sequences of instructions contained in main memory 806 causes processor 804 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage device 810. Volatile media includes dynamic memory, such as main memory 806. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, an EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 802. Transmission media can also take the form of acoustic or light waves, such as those generated during radio-wave and infra-red data communications.

Various forms of media may be involved in carrying one or more sequences of one or more instructions to processor 804 for execution. For example, the instructions may initially be carried on a magnetic disk or solid state drive of a remote computer. The remote computer can load the instructions into its dynamic memory and send the instructions over a network connection. A modem or network interface local to computer system 800 can receive the data. Bus 802 carries the data to main memory 806, from which processor 804 retrieves and executes the instructions. The instructions received by main memory 806 may optionally be stored on storage device 810 either before or after execution by processor 804.

Computer system 800 also includes a communication interface 818 coupled to bus 802. Communication interface 818 provides a two-way data communication coupling to a network link 820 that is connected to a local network 822. For example, communication interface 818 may be an integrated services digital network (ISDN) card, cable modem, satellite modem, or a modem to provide a data communication connection to a corresponding type of telephone line. Wireless links may also be implemented. In any such implementation, communication interface 818 sends and receives electrical, electromagnetic or optical signals that carry digital data streams representing various types of information.

Network link 820 typically provides data communication through one or more networks to other data devices. For example, network link 820 may provide a connection through local network 822 to a host computer 824 or to data equipment operated by an Internet Service Provider (ISP) 826. ISP 826 in turn provides data communication services through the world wide packet data communication network now commonly referred to as the "Internet" 828. Local network 822 and Internet 828 both use electrical, electromagnetic or optical signals that carry digital data streams. The signals through the various networks and the signals on network link 820 and through communication interface 818, which carry the digital data to and from computer system 800, are example forms of transmission media.

Computer system 800 can send messages and receive data, including program code, through the network(s), network link 820 and communication interface 818. In the Internet example, a server 830 might transmit a requested code for an application program through Internet 828, ISP 826, local network 822 and communication interface 818. The received code may be executed by processor 804 as it is received, and/or stored in storage device 810, or other non-volatile storage for later execution.

Figure 9:
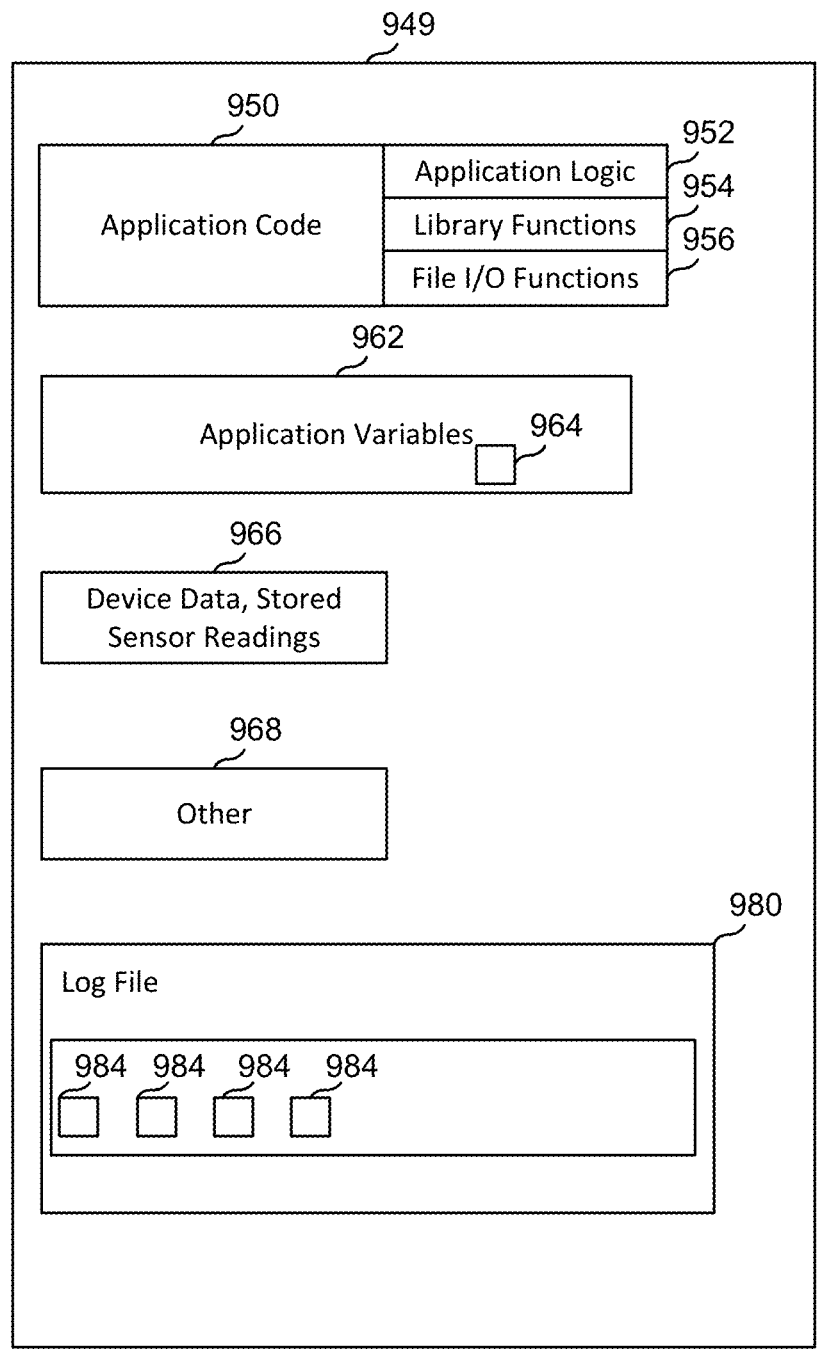
FIG. 9 illustrates structures that might be used by a processor to perform functions described herein and used by the processor to implement elements of the embodiments described herein.

FIG. 9 illustrates structures that might be used by a processor to perform functions described herein and used by the processor to implement elements of the embodiments described herein. For example, where a functional block is referenced, it might be implemented as program code stored in memory. This might be implemented as part of a computer control for a taggant dispenser. The taggant dispenser might be implemented as a stand-alone system, wherein an operator inputs a tag string and the taggant dispenser disperses the appropriate dispersant based on that tag string. The taggant dispenser might be implemented as an integrated system wherein a remote computing platform sends instructions to the taggant dispenser with instructions on which tag string to use, how long to flush, what feedback to provide, etc.

FIG. 9 is a simplified functional block diagram of a storage device 948 having an application that can be accessed and executed by a processor in a computer system. The application can one or more of the applications described herein, running on servers, clients or other platforms or devices and might represent memory of one of the clients and/or servers illustrated elsewhere. Storage device 948 can be one or more memory devices that can be accessed by a processor and storage device 948 can have stored thereon application code 950 that can be configured to store one or more processor readable instructions. The application code 950 can include application logic 952, library functions 954, and file I/O functions 956 associated with the application.

Storage device 948 can also include application variables 962 that can include one or more storage locations configured to receive input variables 964. The application variables 962 can include variables that are generated by the application or otherwise local to the application. The application variables 962 can be generated, for example, from data retrieved from an external source, such as a user or an external device or application. The processor can execute the application code 950 to generate the application variables 962 provided to storage device 948.

Application variables 962 might include operational details needed to perform the functions described herein. Device data 966 might include details such as tag string lookup tables, stored sensor readings and the like and other details needed. One or more memory locations can be configured to store device data 966. Device data 966 can include data that is sourced by an external source, such as a user or an external device.

Storage device 948 can also include a log file 980 having one or more storage locations 984 configured to store results of the application or inputs provided to the application. For example, the log file 980 can be configured to store a history of actions, alerts, error message and the like.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Conjunctive language, such as phrases of the form "at least one of A, B, and C," or "at least one of A, B and C," unless specifically stated otherwise or otherwise clearly contradicted by context, is otherwise understood with the context as used in general to present that an item, term, etc., may be either A or B or C, or any nonempty subset of the set of A and B and C. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present.

The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

Further embodiments can be envisioned to one of ordinary skill in the art after reading this disclosure. In other embodiments, combinations or sub-combinations of the above-disclosed invention can be advantageously made. The example arrangements of components are shown for purposes of illustration and it should be understood that combinations, additions, re-arrangements, and the like are contemplated in alternative embodiments of the present invention. Thus, while the invention has been described with respect to exemplary embodiments, one skilled in the art will recognize that numerous modifications are possible.

For example, the processes described herein may be implemented using hardware components, software components, and/or any combination thereof. The specification and drawings are, accordingly, to be regarded in an illustrative rather than a restrictive sense. It will, however, be evident that various modifications and changes may be made thereunto without departing from the broader spirit and scope of the invention as set forth in the claims and that the invention is intended to cover all modifications and equivalents within the scope of the following claims.

All references, including publications, patent applications, and patents, cited herein are hereby incorporated by reference to the same extent as if each reference were individually and specifically indicated to be incorporated by reference and were set forth in its entirety herein.

What is claimed is:

1. A dispersant system comprising:
a plurality of taggant vessels, wherein a taggant vessel of the plurality of taggant vessels holds a taggant distinct from other taggants of other taggant vessels of the plurality of taggant vessels;
a computer controller, including logic to determine a tag string and convert the tag string into a selection of a taggant set corresponding to selected taggants vessels in the plurality of taggant vessels,
wherein each of the taggant vessels in the plurality of taggant vessels corresponds to a position in the tag string and wherein the computer controller includes logic to allow for flow of a first taggant when a character at the position in the tag string that corresponds to the first taggant is a first value and to block flow of the first taggant when the character at the position in the tag string that corresponds to the first taggant is a second value;

a manifold;

a plurality of computer-controlled valves, coupled to the computer controller, for allowing or blocking a flow of taggants to the manifold according to the taggant set;

a manifold output tube, coupled to the manifold, that outputs a mix of the taggants that flow to form a dispersant formed according to the tag string; and a nozzle for dispersing the dispersant onto an object to be tagged.

2. The dispersant system of claim 1, wherein the taggant comprises a DNA taggant.

3. The dispersant system of claim 2, wherein the DNA taggant comprises a static portion that is present in each taggants in the plurality of taggant vessels and a dynamic portion that is unique such that a first taggant from a first taggant vessel is distinguishable from a second taggant from a second taggant vessel.

4. The dispersant system of claim 1, wherein taggants in the plurality of taggant vessels are mixed with ethanol as a carrier of the taggants.

5. The dispersant system of claim 1, further comprising a nozzle structure that provides for mixing of the dispersant with an atomizing air stream.

6. The dispersant system of claim 1, wherein the computer controller includes logic to flush at least the manifold output tube and the nozzle between changes in the tag string from a first tag string to a second tag string.

7. The dispersant system of claim 1, wherein the first value is a "1" and the second value is a "0" and therefore, when the tag string is a sequence of "1" characters and "0" characters, the taggant set corresponds to positions in the tag string that have a "1" value.

8. The dispersant system of claim 1, wherein the computer controller includes logic to select a first tag string for a first lot of one or more first objects to be tagged with the first tag string and select a second tag string for a second lot of one or more second objects to be tagged with the second tag string, wherein the second tag string is selected based on a Hamming distance from the first tag string.

9. The dispersant system of claim 1, wherein the computer controller includes logic to select tag strings that incorporate redundancy usable to recover from errors or detect errors when the dispersant is sampled for detection of the taggant set used and subsequent determination of the tag string.

10. The dispersant system of claim 1, wherein the computer controller includes logic to select tag strings for distinct lots of one or more objects to be tagged with such that consumption of taggants evens out over the plurality of taggant vessels.

11. The dispersant system of claim 8, wherein the second tag string is selected from a set of unused tag strings and selected to have a low Hamming distance from among the set of unused tag strings.

12. A method comprising:

determining, by logic in a computer controller, a tag string and converting the tag string into a selection of a taggant set corresponding to selected taggants vessels in a plurality of taggant vessels, wherein a taggant vessel of the plurality of taggant vessels holds a taggant distinct from other taggants of other taggant vessels of the plurality of taggant vessels;

allowing or blocking, through a plurality of computer-controlled valves coupled to the computer controller, a flow of taggants to a manifold according to the taggant set;

wherein each of the taggant vessels in the plurality of taggant vessels corresponds to a position in the tag string;

wherein flow of a first taggant is allowed, by logic in the computer controller, when a character at the position in the tag string that corresponds to the first taggant is a first value; and wherein flow of the first taggant is blocked, by logic in the computer controller, when the character at the position in the tag string that corresponds to the first taggant is a second value;

outputting, through a manifold output tube coupled to the manifold, a mix of the taggants that flow to form a dispersant formed according to the tag string; and dispersing, through a nozzle, the dispersant onto an object to be tagged.

13. The method of claim 12, wherein the taggant comprises a DNA taggant.

14. The method of claim 13, wherein the DNA taggant comprises a static portion that is present in each taggants in the plurality of taggant vessels and a dynamic portion that is unique such that a first taggant from a first taggant vessel is distinguishable from a second taggant from a second taggant vessel.

15. The method of claim 12, wherein taggants in the plurality of taggant vessels are mixed with ethanol as a carrier of the taggants.

16. The method of claim 12, further comprising mixing the dispersant with an atomizing air stream.

17. The method of claim 12, further comprising flushing at least the manifold output tube and the nozzle between changes in the tag string from a first tag string to a second tag string.

18. The method of claim 12, wherein the first value is a "1" and the second value is a "0" and therefore, when the tag string is a sequence of "1" characters and "0" characters, the taggant set corresponds to positions in the tag string that have a "1" value.

19. The method of claim 12, further comprising selecting a first tag string for a first lot of one or more first objects to be tagged with the first tag string and select a second tag string for a second lot of one or more second objects to be tagged with the second tag string, wherein the second tag string is selected based on a Hamming distance from the first tag string, selecting tag strings that incorporate redundancy usable to recover from errors or detect errors when the dispersant is sampled for detection of the taggant set used and subsequent determination of the tag string, or selecting tag strings for distinct lots of one or more objects to be tagged with such that consumption of taggants evens out over the plurality of taggant vessels.

* * * * *